US009084677B2

(12) United States Patent
Cartledge et al.

(10) Patent No.: US 9,084,677 B2
(45) Date of Patent: Jul. 21, 2015

(54) METHOD AND SYSTEM FOR LONG TERM ADJUSTMENT OF AN IMPLANTABLE DEVICE

(75) Inventors: Richard G. Cartledge, Boca Raton, FL (US); John P. Cartledge, Boca Raton, FL (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 105 days.

(21) Appl. No.: 13/055,044

(22) PCT Filed: Jul. 29, 2009
(Under 37 CFR 1.47)

(86) PCT No.: PCT/US2009/052053
§ 371 (c)(1),
(2), (4) Date: May 3, 2011

(87) PCT Pub. No.: WO2010/014671
PCT Pub. Date: Feb. 4, 2010

(65) Prior Publication Data
US 2011/0202130 A1    Aug. 18, 2011

Related U.S. Application Data

(60) Provisional application No. 61/084,446, filed on Jul. 29, 2008.

(51) Int. Cl.
*A61F 2/24*    (2006.01)

(52) U.S. Cl.
CPC ............ *A61F 2/2448* (2013.01); *A61F 2/2445* (2013.01); *A61F 2/2466* (2013.01); *A61F 2210/009* (2013.01); *A61F 2250/0001* (2013.01); *A61F 2250/0004* (2013.01)

(58) Field of Classification Search
USPC ................................. 623/2.36–2.38
See application file for complete search history.

(56) References Cited

U.S. PATENT DOCUMENTS 5,171,266 A    12/1992    Wiley et al.
5,800,533 A    9/1998    Eggleston et al.
(Continued)

FOREIGN PATENT DOCUMENTS

EP    1611868 A2    1/2006

OTHER PUBLICATIONS

European Search Report for Application No. EP09803526 dated Jul. 19, 2012.
(Continued)

*Primary Examiner* — Andrew Iwamaye
*Assistant Examiner* — Leslie Lopez
(74) *Attorney, Agent, or Firm* — Lerner, David, Littenberg, Krumholz & Mentlik, LLP

(57) ABSTRACT

The present invention is directed to methods and systems for adjusting an implant, such as a mitral valve ring, over the long term without having to enter a patient's body. The long term adjustment system can include a magnet, or other magnetic material, that is functionally connected to the adjustment mechanism of an adjustable implant. The long term adjustment system can be activated by placing an activating magnet near the area of the patient's body where the adjustable implant is located and positioning the activating magnet so that an attractive force is generated between the activating magnet and the magnet that is functionally connected to the adjustable implant. Due to the attractive force between the two magnets, rotation of the magnet outside the patient's body will adjust the size and/or shape of the implant.

12 Claims, 18 Drawing Sheets

(56) References Cited

U.S. PATENT DOCUMENTS

| | | |
|---|---|---|
| 7,175,660 B2 | 2/2007 | Cartledge et al. |
| 7,297,150 B2 | 11/2007 | Cartledge et al. |
| 7,455,690 B2 | 11/2008 | Cartledge et al. |
| 2004/0010219 A1* | 1/2004 | McCusker et al. ............ 604/9 |
| 2006/0106405 A1 | 5/2006 | Fann et al. |
| 2006/0241748 A1* | 10/2006 | Lee et al. .............. 623/2.37 |
| 2007/0016287 A1 | 1/2007 | Cartledge et al. |
| 2007/0135913 A1 | 6/2007 | Moaddeb et al. |
| 2007/0142907 A1 | 6/2007 | Moaddeb et al. |
| 2007/0233239 A1 | 10/2007 | Navia et al. |
| 2007/0299543 A1 | 12/2007 | Cartledge et al. |
| 2008/0027483 A1 | 1/2008 | Cartledge et al. |
| 2008/0097496 A1* | 4/2008 | Chang et al. ............ 606/157 |
| 2008/0109076 A1 | 5/2008 | Cartledge et al. |
| 2008/0127689 A1 | 6/2008 | McCusker et al. |
| 2008/0306586 A1 | 12/2008 | Cartledge et al. |
| 2009/0125102 A1 | 5/2009 | Cartledge et al. |
| 2009/0234404 A1 | 9/2009 | Fitzgerald et al. |
| 2010/0305609 A1 | 12/2010 | Cartledge et al. |
| 2011/0009956 A1 | 1/2011 | Cartledge et al. |
| 2011/0022168 A1 | 1/2011 | Cartledge |
| 2011/0066231 A1 | 3/2011 | Cartledge et al. |
| 2011/0093062 A1 | 4/2011 | Cartledge et al. |
| 2011/0196480 A1 | 8/2011 | Cartledge |
| 2011/0208295 A1 | 8/2011 | Cartledge et al. |
| 2011/0257633 A1 | 10/2011 | Cartledge et al. |

OTHER PUBLICATIONS

International Search Report, ISA/US, Sep. 21, 2009 (attached to published International application received from International Bureau).

U.S. Appl. No. 13/123,768.

Letter dated Jan. 27, 2011 from Richard H. Levinstein, Esq.

* cited by examiner

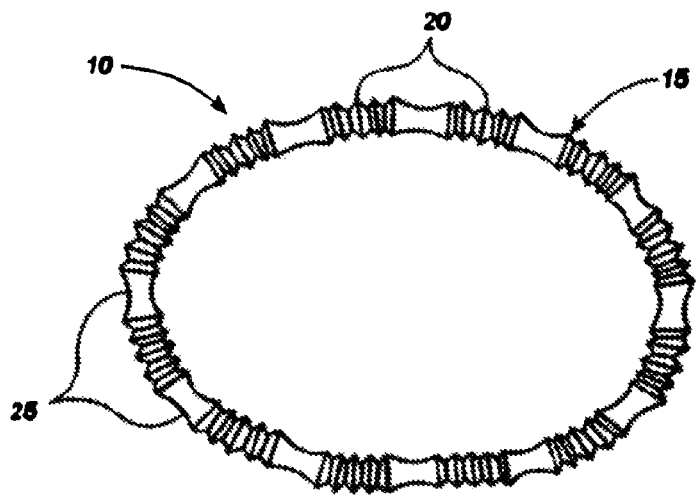
Fig. 1
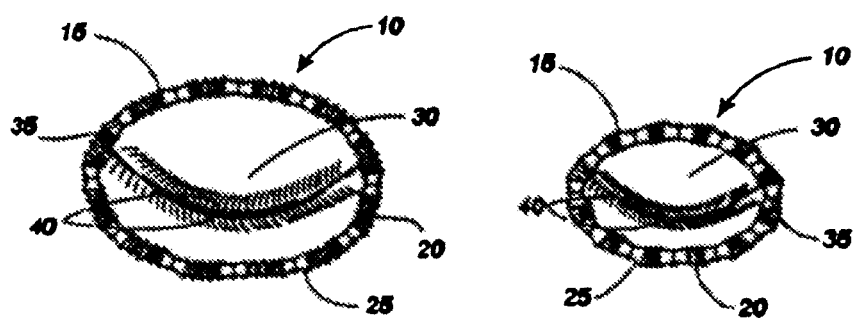
Fig. 2  Fig. 3

METHOD AND SYSTEM FOR LONG TERM ADJUSTMENT OF AN IMPLANTABLE DEVICE

CROSS REFERENCE TO RELATED APPLICATIONS

The present application is a national phase entry under 356 U.S.C. §371 of International Application No. PCT/US2009/52053 filed Jul. 29, 2009, which claims priority from U.S. Provisional Patent Application No. 61/084,446, filed on Jul. 29, 2008, all of which are hereby incorporated herein by reference.

STATEMENT REGARDING SPONSORED RESEARCH OR DEVELOPMENT

Not Applicable.

REFERENCE TO SEQUENCE LISTING

Not Applicable.

TECHNICAL FIELD

The present invention relates generally to methods and systems for the long term adjustment (i.e., months to years after implantation) of an annular implant for controlling the size and/or shape of an anatomical orifice or lumen.

BACKGROUND

Many anatomic structures in the mammalian body are hollow passages with walls of tissue that define a central lumen, which serves as a conduit for blood, other physiologic fluids, nutrient matter, or waste matter passing within the structure. In many physiologic settings, dysfunction may result from a structural lumen which is either too large or too small. In most such cases, dysfunction can be relieved by interventional changes in the size and/or shape of the lumen.

As a result, there is often a need to adjust the size and/or shape of the internal circumference of an orifice or other open anatomic structure in order to achieve a desired physiologic effect. Such surgical procedures often require interruption of the normal physiologic flow of blood, other physiologic fluids, or other structural contents through the orifice or structure. However, the exact amount of change in the size and/or shape of the orifice or structure needed to obtain the desired effect usually cannot be fully appreciated until physiologic flow through the orifice or structure is resumed. It would be advantageous, therefore, to have an adjustable means for achieving this change in the size and/or shape of an orifice or structure, such that the adjustment could be made after its implantation, and after the resumption of normal physiologic flow in situ.

One example of dysfunction within an anatomic lumen is in the area of cardiac surgery, and, specifically, valvular repair. Due to the difficulties in engineering a perfect prosthetic heart valve, there has been a growing interest in repairing a patient's native valve. In particular, mitral valve repair has become one of the most rapidly growing areas in adult cardiac surgery today.

Historically, most valvular pathology was secondary to rheumatic heart disease, a result of a streptococcal infection, most commonly affecting the mitral valve, followed by the aortic valve, and least often the pulmonic valve. The results of the infectious process are mitral and aortic stenosis, followed by mitral and aortic insufficiency. With the advent of better antibiotic therapies, the incidence of rheumatic heart disease is on the decline, and accounts for a smaller percentage of valvular heart conditions in the developed world of the present day. Commissurotomy of rheumatic mitral stenosis was an early example of commonly practiced mitral valve repair outside the realm of congenital heart defects. However, repairing rheumatic insufficient valves did not provide good results because of the underlying valve pathology and the progression of disease.

Most mitral valve disease, other than rheumatic, results in valvular insufficiency, which is generally amenable to repair. Chordae rupture is a common cause of mitral insufficiency, resulting in a focal area of regurgitation. One of the first successful and accepted surgical repairs was for ruptured chordae of the posterior mitral leaflet. The technical feasibility of this repair, its reproducibility, and its long-term durability led pioneer surgeons in the field of mitral valve repair to attempt repairs of other valve pathologies.

Mitral valve prolapse is a fairly common condition that leads over time to valvular insufficiency. In this disease, the plane of coaptation of the anterior and posterior leaflets is "atrialized" relative to a normal valve. This problem may readily be repaired by restoring the plane of coaptation into the ventricle.

The papillary muscles within the left ventricle support the mitral valve and aid in its function. Papillary muscle dysfunction, whether due to infarction or ischemia from coronary artery disease, often leads to mitral insufficiency (commonly referred to as ischemic mitral insufficiency). Within the scope of mitral valve disease, this is the most rapidly growing area for valve repair. Historically, only patients with severe mitral insufficiency had their mitral valve repaired or replaced, but there is increasing support in the surgical literature to support valve repair in patients with moderate insufficiency that is attributable to ischemic mitral insufficiency. Early aggressive valve repair in this patient population has been shown to increase survival and improve long-term ventricular function.

In addition, in patients with dilated cardiomyopathy, the etiology of mitral insufficiency is the lack of coaptation of the valve leaflets from a dilated ventricle. The resultant regurgitation is due to the lack of coaptation of the leaflets. There is a growing trend to repair these valves, thereby repairing the insufficiency and restoring ventricular geometry, thus improving overall ventricular function.

Two essential features of mitral valve repair are to fix primary valvular pathology (if present) and to support the annulus or reduce the annular dimension using a prosthesis that is commonly in the form of a ring or band. The problem encountered in mitral valve repair is the surgeon's inability to fully assess the effectiveness of the repair until the heart has been fully closed, and the patient is weaned off cardiopulmonary bypass. Once this has been achieved, valvular function can be assessed in the operating room using trans-esophageal echocardiography (TEE). If the implant used to reduce the annulus is larger than the ideal size, mitral insufficiency may persist. If the implant is too small, mitral stenosis may result. In such cases, the surgeon must re-arrest the heart, reopen the heart, and then re-repair or replace the valve. This increases overall operative, anesthesia, and bypass times, and therefore increases the overall operative risks. The need exists, therefore, for an adjustable implant that would allow a surgeon to adjust the size and/or shape of annulus in situ in a beating heart under TEE guidance, or other diagnostic modalities, to achieve optimal valvular sufficiency and function.

Furthermore, it is not always possible to determine whether optimal valvular sufficiency and function has been achieved until some extended period of time after the valve has been repaired, and thus later adjustment of the implant may be needed. Also, there are instances in which mitral insufficiency reoccurs and further adjustment of the size and/or shape of the mitral valve becomes necessary. As a result, there also exists a need in the art for methods and systems that allow for the long term adjustment (i.e., months to years after implantation) of an implantable device, in a non-invasive manner.

SUMMARY OF THE INVENTION

Accordingly, the present invention is directed to methods and systems for adjusting an implant, such as a mitral valve ring, over the long term (i.e., months to years after implantation) without having to enter a patient's body. In one embodiment of the present invention, a long term adjustment system includes a magnet, or other magnetic material, that is functionally connected to the adjustment mechanism of an adjustable implant. The long term adjustment system can be activated, without any entry into a patient's body, by placing an activating magnet near the area of the patient's body where the adjustable implant is located and positioning the activating magnet so that an attractive force is generated between the activating magnet and the magnet, or other magnetic material, that is functionally connected to the adjustable implant. Due to the attractive force between the two magnets, rotation of the magnet outside the patient's body will cause a corresponding rotation of the magnet functionally connected to the adjustable implant, which in turn will adjust the size and/or shape of the implant. The above-described system is just one example of the present invention, which can vary in other embodiments.

BRIEF DESCRIPTION OF THE DRAWINGS

The accompanying drawings, which are included to provide further understanding of the invention and are incorporated in and constitute part of this specification, illustrate embodiments of the invention and together with the description serve to explain the principles of the invention. In the drawings:

FIG. 1 is a front view of an embodiment of an implant for reducing the circumference of an anatomic orifice.

FIG. 2 is a front view of the implant of FIG. 1 secured to the annulus of a mitral valve, with the implant in an expanded position.

FIG. 3 is a front view of the implant of FIG. 1 secured to the annulus of a mitral valve, with the implant in a contracted position to reduce the size of the heart valve opening.

DETAILED DESCRIPTION OF THE PREFERRED EMBODIMENTS

Figure 4:
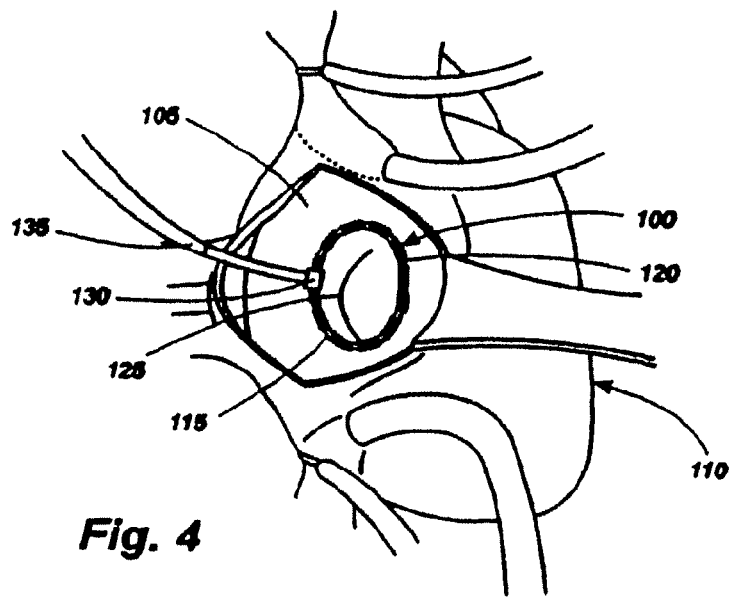
FIG. 4 is a perspective view of an embodiment of an implant for reducing the circumference of an anatomic orifice, inserted through an open operative cardiac incision and secured around the mitral valve.

Reference will now be made in detail to the preferred embodiments of the present invention, examples of which are illustrated in the accompanying drawings. Throughout the following drawings, like numerals indicate like elements.

FIG. 1 shows one embodiment of the present invention, in which implant 10 comprises an implant body 15. The implant body 15 may be provided in a shape and size determined by the anatomic needs of an intended native recipient anatomic site within a mammalian patient. Such a native recipient anatomic site may be, by way of illustration and not by way of limitation, a heart valve, the esophagus near the gastro-esophageal junction, the anus, or other anatomic sites within a mammalian body that are creating a dysfunction that might be relieved by an implant capable of changing the size and shape of that site and maintaining a desired size and shape after surgery.

Still referring to FIG. 1, the implant body 15 is provided with adjustable corrugated sections 20 alternating with intervening grommet-like attachment means 25 having narrowed intermediate neck portions. As shown in FIGS. 2 and 3, the implant body 15 may be secured to the annulus of a heart valve 30 by a fixation means such as a suture 35 secured over or through the attachment means 25. The corrugated sections 20 fold and unfold as the circumference of the implant body 15 shortens or lengthens. Adjustment of the implant 10 in situ may decrease the overall size of the heart valve 30, increasing coaptation of the valve leaflets 40, and changing the configuration from that shown in FIG. 2 to that shown in FIG. 3.

Figure 5:
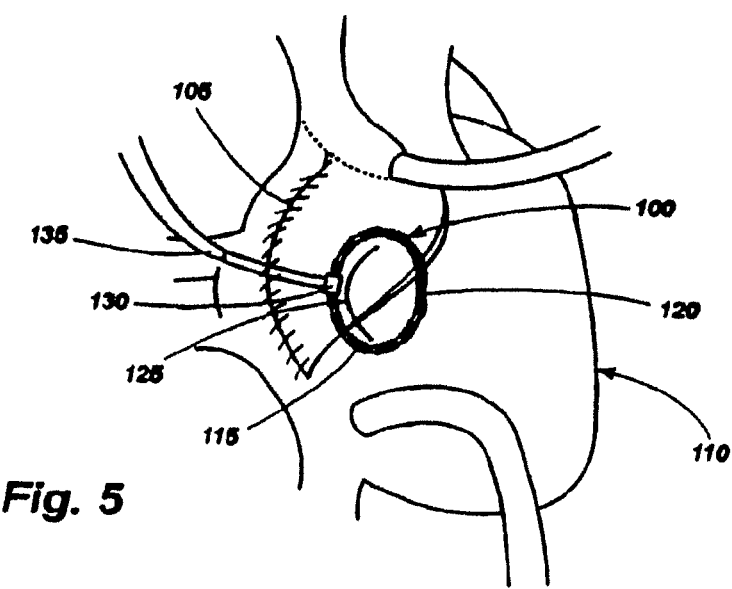
FIG. 5 is a perspective view of the implant of FIG. 4, showing the cardiac incision closed and an adjustment tool extending through the closed incision.

FIGS. 4 and 5 show another embodiment of the present invention. FIG. 4 shows an open operative cardiac incision 105 in a heart 110, and FIG. 5 shows a closed cardiac incision 105 in a heart 110. As shown in FIG. 4, the adjustable implant 100 of the present invention comprises an implant body 115 with attachment means 120 that allow fixation to the annulus of a mitral valve 125. The adjustable implant 100 is further provided with an adjustment means 130 that is controlled by an attached or coupled adjustment tool 135. After closure of the cardiac incision 105 as shown in FIG. 5, the adjustment tool 135 remains attached or coupled to the adjustment means 130, so that the size and shape of the adjustable implant 100 may be further affected after physiologic flow through the heart 110 is resumed, but while a chest incision is still open. Once the desired shape and function are achieved, the adjustment tool 135 may be disengaged from the adjustment means 130 and withdrawn from the cardiac incision 105. In various embodiments of the present invention, the adjustment means 130 may be configured and placed to allow retention or reintroduction of the adjustment tool 135 for adjustments after closure of the chest incision.

To use the adjustable implant 100 of FIGS. 4 and 5, a physician makes the open cardiac incision 105 in the heart 110, as shown in FIG. 4, in the conventional manner. The adjustable implant 100, mounted at the forward end of adjustment tool 135, is then advanced through the incision 105 and sutured to the annulus of the mitral valve 125. The adjustment tool 135 is then manipulated (e.g., rotated), depending upon the design of the adjustment means 130, to cause the adjustment means 130 to reduce the size of the implant body 115, and hence the underlying mitral valve 125 to which it is sutured, to an approximate size. The cardiac incision 105 can then be closed, as shown in FIG. 5, leaving the adjustment tool 135 extending through the incision for post-operative adjustment. Once normal flow of blood through the heart 110 has resumed, but before the chest incision is closed, further adjustments to the size of the adjustable implant 100, and thus the mitral valve 125, can be made by manipulating the adjustment tool 135.

Figure 6:
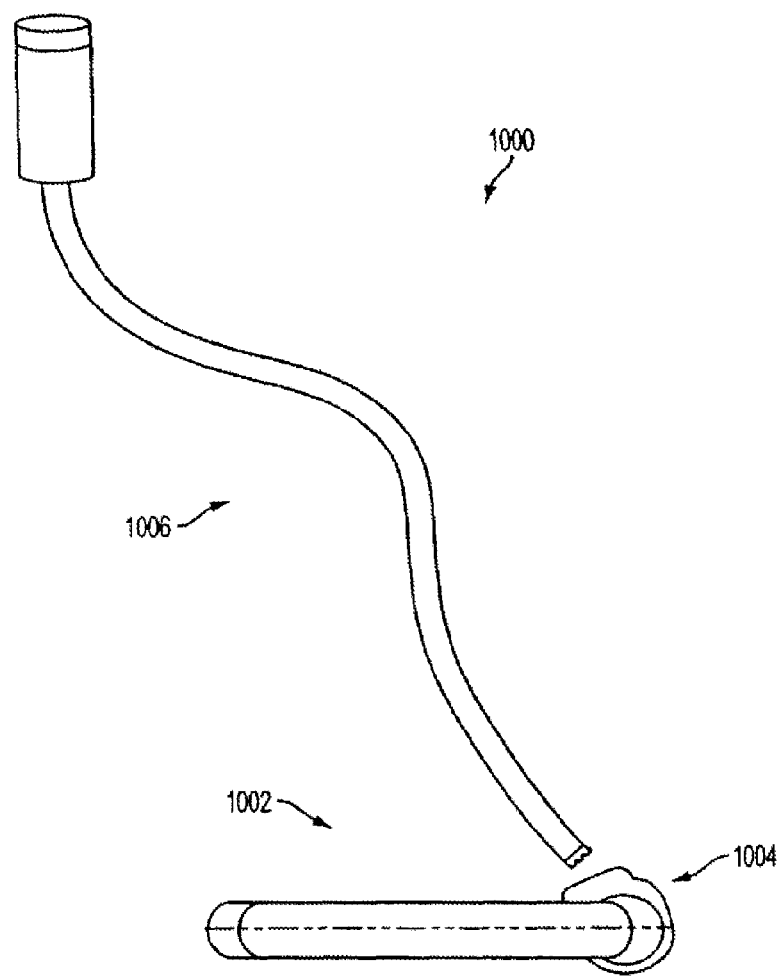
FIG. 6 is a schematic view of an embodiment of an implantable device for reducing the circumference of an anatomic orifice.

In another embodiment of the present invention, illustrated in FIG. 6, an implantable device system 1000 for controlling at least the size or shape of an anatomical structure or lumen comprises an implantable device 1002 and an adjustment tool 1006. The implantable device 1002 has an adjustable member 1004 configured to adjust the dimensions of the implantable device 1002. While the implantable device 1002 is generally shown in the following figures to have a "D-shaped" configuration, it should be understood that other shapes can be used in accordance with the embodiments of the present invention.

The adjustment tool 1006 may be an elongated tool with a proximal end and a distal end. The distal end can be releasably attached to the adjustable member 1004 of the implantable device 1002. The adjustment tool 1006 may extend from its distal end, which can be coupled to the adjustable member 1004, to its proximal end, which may include a control interface (e.g., a handle) that is preferably located outside of a patient's body. The adjustment tool 1006 can adjust the implantable device 1002 by narrowing or widening the dimensions of the implantable device 1002. In some embodiments, the adjustment tool 1006 is at least partially hollow, and in one specific embodiment, is at least 50% hollow.

Figure 7A:
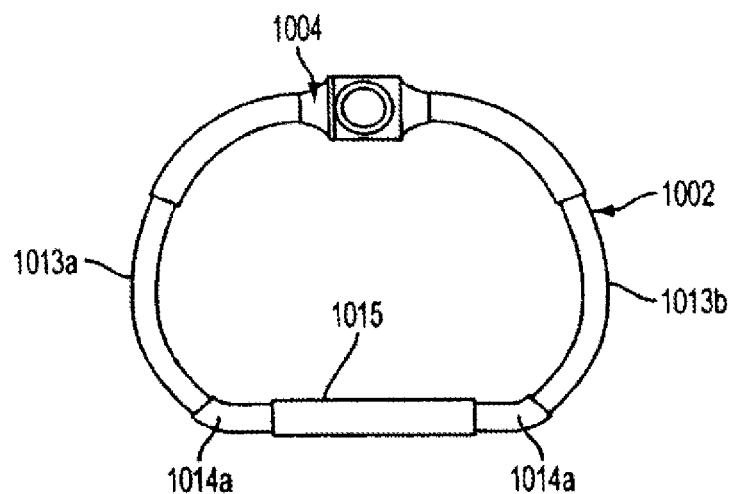
FIG. 7A is a schematic view of an embodiment of an implantable device for reducing the circumference of an anatomic orifice.
Figure 7B:
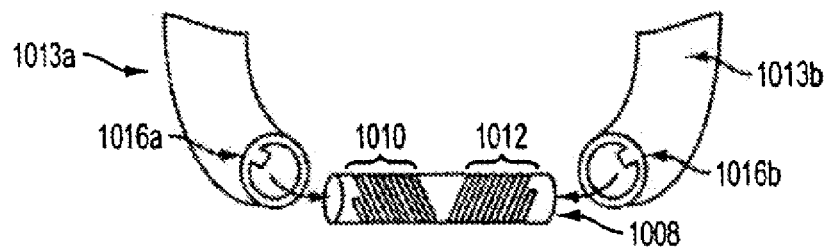
FIG. 7B is a schematic view of a threaded member in the implantable device of FIG. 7A.

FIG. 7A shows the implantable device 1002, without an optional flexible outer tube and fabric sheath. The implantable device 1002 includes an adjustable member 1004, adjustable tube portions 1013a and 1013b, which slide within hollow tube portions 1014a and 1014b, and retaining tube 1015. The hollow tube portions 1014a and 1014b are relatively rigid so as to maintain the curvature of the adjustable tube portions 1013a and 1013b, regardless of the adjustment position. FIG. 7B shows a disassembled portion of the implantable device 1002 with retaining tube 1015 removed. As shown in FIG. 7B, in some embodiments, the implantable device 1002 includes a threaded rod 1008, which can be threaded with right-hand helical grooves 1010 and left-hand helical grooves 1012. Other embodiments may include a threaded rod 1008 with helical grooves in a single direction (i.e., all right-hand grooves or all left-hand grooves). The threaded rod 1008 may be a rigid material, such as titanium, stainless steel, or a polymer. The adjustable tube portions 1013a and 1013b enclose at least a portion of the helical grooves 1010 and 1012, so that pins 1016a and 1016b or other protuberances on the inside diameter of the adjustable tube portions 1013a and 1013b are engaged by the helical grooves 1010 and 1012, respectively. In other embodiments, the pins 1016a and 1016b may be replaced by threads along the inside diameter of the adjustable tube portions 1013a and 1013b. Further, the helical grooves 1010 and 1012 may have single channels or multiple channels to engage single pins 1016a and 1016b or multiple pins.

Figure 8:
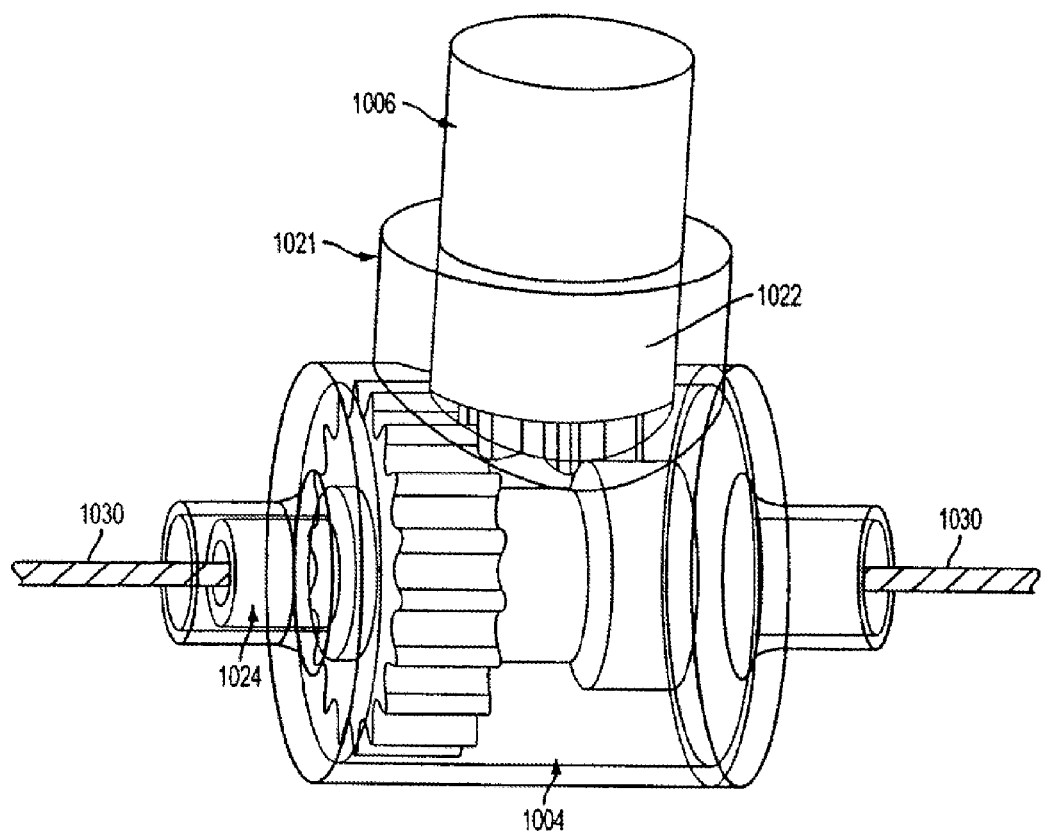
FIG. 8 is a schematic view of an embodiment of an adjustable member of the present invention, with the distal tip of the adjustment tool coupled to the adjustment member.
Figure 9:
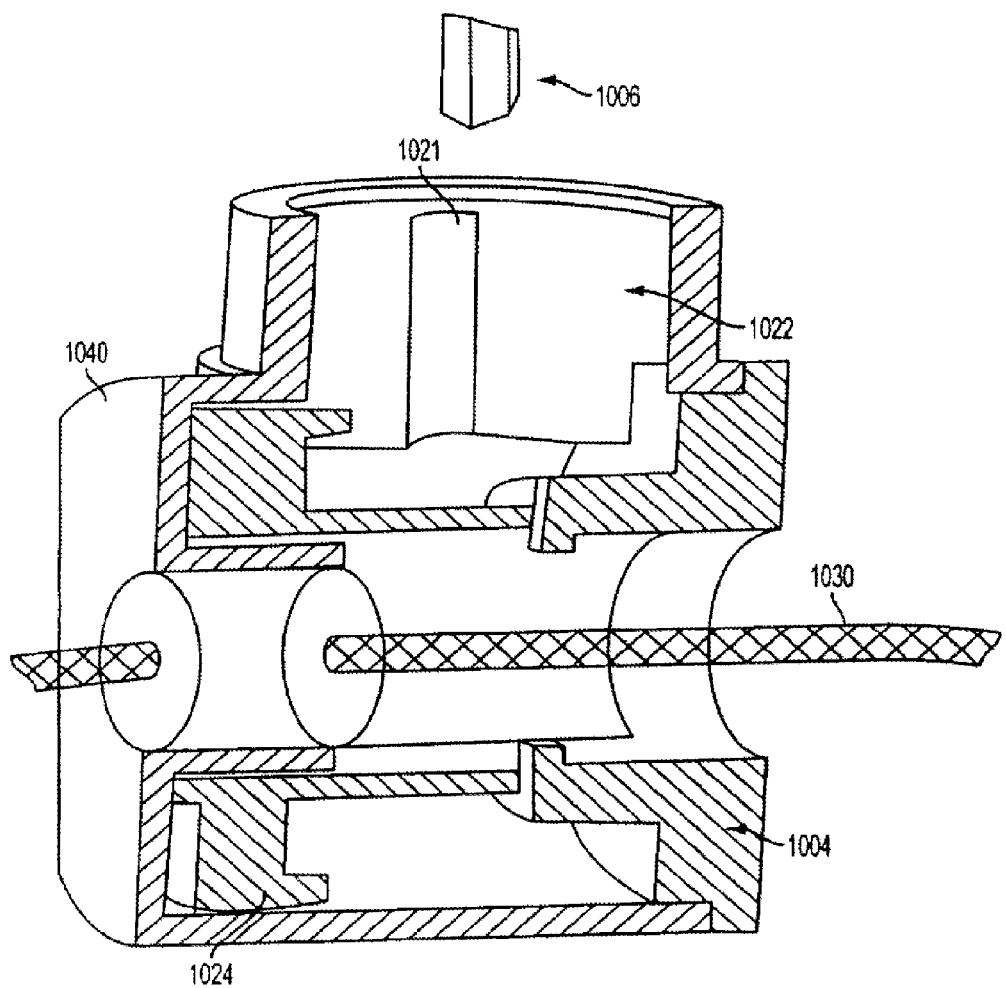
FIG. 9 is a schematic view of an embodiment of an adjustable member of the present invention having an integrated pinion gear.

As shown in FIGS. 8 and 9, the adjustable member 1004 may include a pinion gear 1022, which may be integral to a docking port 1021, and a crown gear 1024. FIG. 8 provides an isometric view of the adjustable member 1004, and FIG. 9 provides a cut-away view of the adjustable member 1004. As shown in FIGS. 8 and 9, the pinion gear 1022 engages the crown gear 1024, and rotation of the crown gear 1024 imparts rotation to an inner cable 1030 in the same direction. In some embodiments, the adjustment tool 1006, when coupled to the docking port 1021, can rotate the pinion gear 1022. In other embodiments, the pinion gear 1022 may be eliminated from the adjustable member 1004, and the distal tip of the adjustment tool 1006 may serve as the pinion gear when the adjustment tool 1006 is coupled to the docking port 1021.

Figure 10:
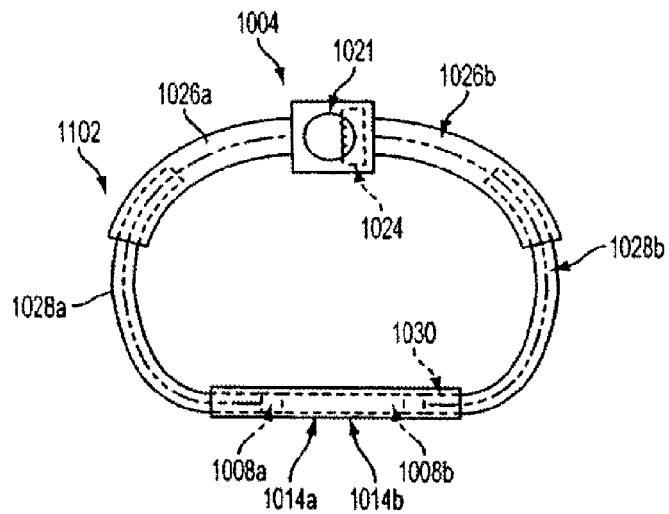
FIG. 10 is a schematic view of an embodiment of an implantable device of the present invention with an outer tubing and an inner tubing in a relative first position.
Figure 11:
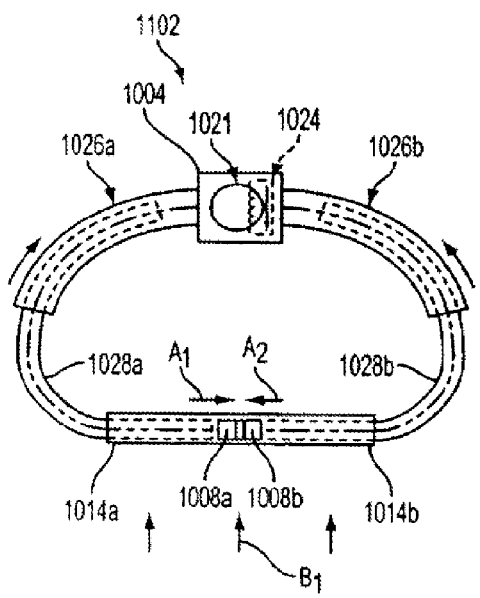
FIG. 11 is a schematic view of an embodiment of an implantable device of the present invention with an outer tubing and an inner tubing in a relative second position.
Figure 12:
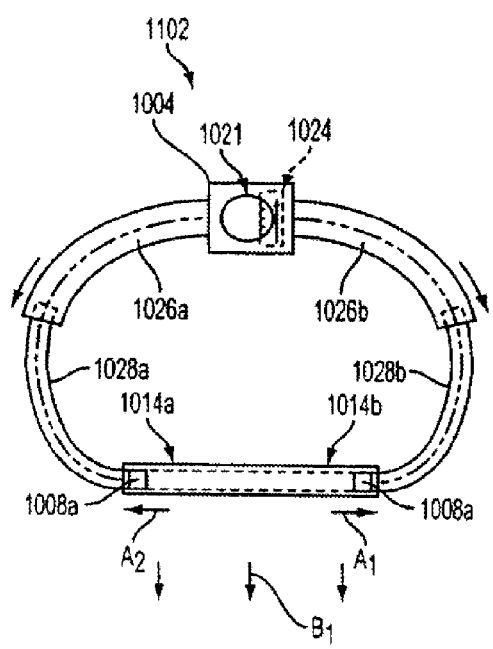
FIG. 12 is a schematic view of an embodiment of an implantable device of the present invention with an outer tubing and an inner tubing in a relative third position.

FIGS. 10-12 show the operation of one embodiment of the present invention. As shown in FIG. 10, an adjustable member 1004 of implantable device 1102 includes a docking port 1021 to receive a distal end of an adjustment tool 1006 (shown in FIG. 6). In one embodiment of the present invention, the implantable device 1102 includes a set of inner tubing 1028a and 1028b and a set of outer tubing 1026a and 1026b, which can move relative to each other. The ends of the inner tubing 1028a and 1028b that do not engage the outer tubing 1026a and 1026b are secured to a set of hollow tube portions 1014a and 1014b, so that the inner tubing 1028a and 1028b does not move relative to the hollow tube portions 1014a and 1014b. Although the hollow tube portions 1014a and 1014b may be separate pieces that are permanently abutted when assembled, in some embodiments, the hollow tube portions 1014a and 1014b may be formed from a single tubing piece. An inner cable 1030 passes through the various tubing. The rigidity of the hollow tube portions 1014a and 1014b can be used to maintain a shape of the implantable device 1102 in certain dimensions, so that adjustment of the implantable device 1102 can be restricted to a preferred dimension, such as an anterior-posterior dimension.

In FIG. 10, the implantable device 1102 is shown generally at the middle of its adjustment range. The outer tubing 1026a and 1026b is affixed to the adjustable member 1004 and extends along a portion of the circumference of the implantable device 1102. The inner tubing 1028a and 1028b is affixed to the hollow tube portions 1014a and 1014b, respectively. Similar to the single threaded rod 1008 of FIG. 7B, threaded rods 1018a and 1018b sit inside the hollow tube portions 1014a and 1014b and are threadedly engaged therewith. The threaded rods 1018a and 1018b may be a rigid material, such as titanium, stainless steel, or a polymer. The hollow tube portions 1014a and 1014b enclose the threaded rods 1018a and 1018b, such that rotation of the threaded rods 1018a and 1018b causes them to move axially within the hollow tube portions 1014a and 1014b. The threaded rod 1018a may have right-hand threads, and the threaded rod 1018b may have left-hand threads. In other embodiments of the present invention, the threaded rods 1018a and 1018b may have threads in a single direction (e.g., all right-hand threads or all left-hand threads).

Still referring to FIG. 10, a crown gear 1024 and one end of each of the threaded rods 1018a and 1018b are attached to the inner cable 1030. The inner cable 1030 may be a cable or tube of any material with sufficient flexibility to conform to a shape of the implantable device 1102 while translating torque. For example, suitable material for the inner cable 1030 may include titanium or stainless steel. As previously shown in FIGS. 8 and 9, rotation of the crown gear 1024 imparts rotation to the cable 1030 in the same direction.

According to one embodiment of the present invention, when the handle of the adjustment tool 1006 (shown in FIG. 6) is rotated clockwise in the docking port 1021, it causes clockwise rotation of the pinion gear 1022 (shown in FIG. 8). Rotation of the pinion gear 1022 causes rotation of the crown gear 1024. As shown in FIG. 11, rotation of the crown gear 1024 causes rotation of the inner cable 1030, which in turn imparts rotational movement to each of the threaded rods 1018a and 1018b. The rotation applied to the threaded rods 1018a and 1018b causes them to advance into their respective hollow tube portions 1014a and 1014b in the directions $A_1$ and $A_2$, shown in FIG. 11. As the threaded rods 1018a and 1018b advance toward the middle of the hollow tube portions 1014a and 1014b, the overall circumference of the implantable device 1102 is reduced. Advancing the threaded rods 1018a and 1018b drives the inner cable 1030 into the hollow tube portions 1014a and 1014b. Translation of the inner cable 1030 into the hollow tube portions 1014a and 1014b causes the hollow tube portions 1014a and 1014b to move towards the adjustable member 1004 in the direction $B_1$, shown in FIG. 11. The inner tubing 1028a and 1028b then slides into the outer tubing 1026a and 1026b, to accommodate the movement of the inner cable 1030.

According to one embodiment of the present invention, when the handle of the adjustment tool 1006 (shown in FIG. 6) is rotated counter-clockwise in the docking port 1021, it causes counter-clockwise rotation of the pinion gear 1022 (shown in FIG. 8). Rotation of the pinion gear 1022 causes rotation of the crown gear 1024. As shown in FIG. 12, rotation of the crown gear 1024 causes rotation of the inner cable 1030, which imparts rotational movement to each of the threaded rods 1018a and 1018b. The rotation applied to the threaded rods 1018a and 1018b causes them to begin to withdraw from their respective hollow tube portions 1014a and 1014b in the directions $A_1$ and $A_2$, shown in FIG. 12. As the threaded rods 1018a and 1018b withdraw from the middle of the hollow tube portions 1014a and 1014b, the overall circumference of the implantable device 1102 is increased. Withdrawal of the threaded rods 1018a and 1018b pushes the inner cable 1030 out of the hollow tube portions 1014a and 1014b. Translation of the inner cable 1030 out of the hollow tube portions 1014a and 1014b causes the hollow tube portions 1014a and 1014b to move away from adjustable member 1004 in the direction $B_2$, shown in FIG. 12. To accommodate the movement of the inner cable 1030, the inner tubing 1028a and 1028b telescopes out of the outer tubing 1026a and 1026b.

FIGS. 13-20 show several embodiments of a long term adjustment system for an implantable device. The long term adjustment system can remain in the patient's body indefinitely, so that it can be used to adjust the size and/or shape of an implantable device months, or even years, after implantation. The long term adjustment system shown in FIGS. 13-20 and described in detail below can be used to adjust the size and/or shape of an implantable device without any invasion into a patient's body.

Figure 13:
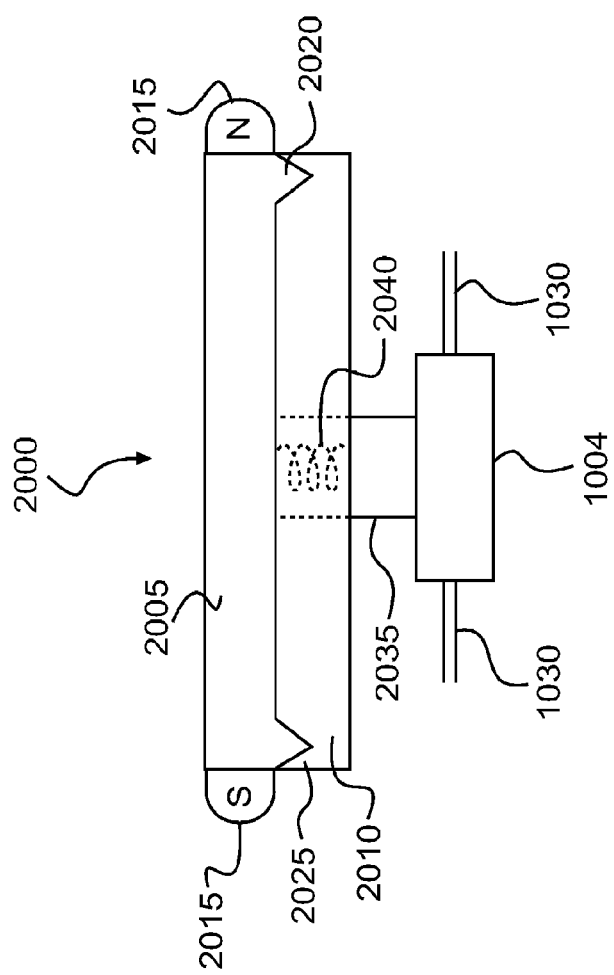
FIG. 13 is a schematic view of an embodiment of a long term adjustment system of the present invention in a locked position.

FIG. 13 shows one embodiment of a long term adjustment system 2000 that comprises an upper element 2005 and a lower element 2010. The upper element 2005 may include a magnet 2015 and retention pins 2020. In preferred embodiments, the magnet 2015 can also be magnetic material, such as pieces of ferrous, for example. The lower element 2010 may include retention holes 2025. The upper element 2005 is rotatably connected to an adjustable member 1004 of an implantable device 1102 (shown in FIGS. 10-12) via a shaft 2035, which passes through the lower element 2010. The connection between the shaft 2035 and the adjustable member 1004 is shown in greater detail in FIG. 16. The shaft 2035 includes a spring 2040 that is configured so that the force of the spring 2040 keeps the long term adjustment system 2000 in a locked position. The long term adjustment system 2000 is in the locked position when the retention pins 2020 of the upper element 2005 are engaged with the retention holes 2025 of the lower element 2010, as shown in FIG. 13. When in the locked position, the upper element 2005 cannot move relative to the lower element 2010, and thus cannot activate the adjustable member 1004 of the implantable device 1102 (shown in FIGS. 10-12). Although not shown in FIG. 13, the long term adjustment system 2000 can have an optional outside covering.

Figure 14:
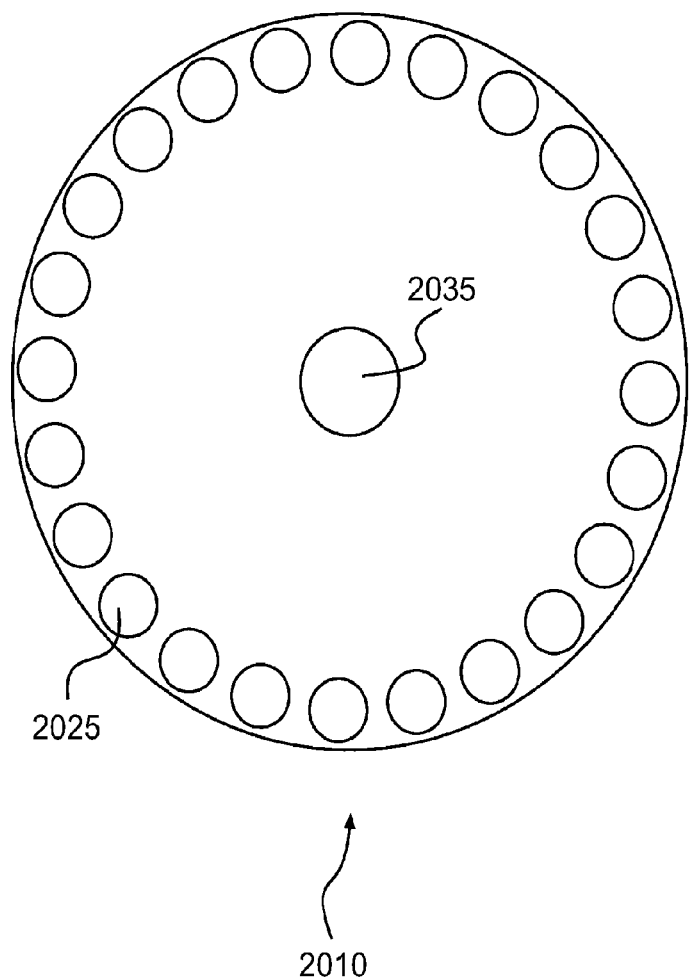
FIG. 14 is a schematic view of an embodiment of a lower element of the long term adjustment system in FIG. 13.

FIG. 14 shows a more detailed view of the lower element 2010 with retention holes 2025 and shaft 2035.

Figure 15:
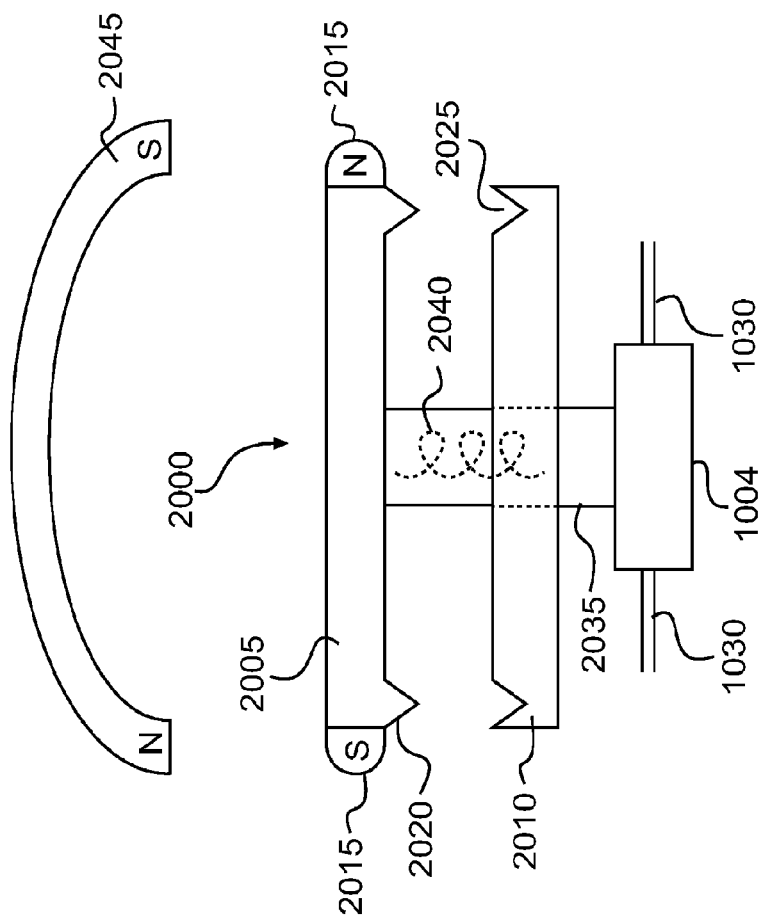
FIG. 15 is a schematic view of an embodiment of a long term adjustment system of the present invention in an activated position.

FIG. 15 shows the long term adjustment system 2000 in an activated position. The long term adjustment system 2000 can be activated, without any entry into a patient's body, by placing an activating magnet 2045 near the area of the patient's body where the long term adjustment system 2000 is located and positioning the activating magnet 2045 so that an attractive force is generated between the activating magnet 2045 and the magnet 2015 in the upper element 2005. This positioning can be achieved using echocardiography or other known diagnostic modalities. The activating magnet 2045 can be any magnet that will attract the magnet 2015 in the upper element 2005 with a force sufficient to overcome the force of the spring 2040. As a result, when the activating magnet 2045 is properly positioned, the attractive force generated by the activating magnet 2045 will pull the upper element 2005 away from the lower element 2010, thus disengaging the retention pins 2020 from the retention holes 2025. Once the upper element 2005 has been disengaged from the lower element 2010, rotating the activating magnet 2045 outside the patient's body will cause a corresponding rotation of the upper element 2005 and the shaft 2035. As shown in more detail in FIG. 16, the rotation of the upper element 2005 and the shaft 2035 will cause the adjustable member 1004 to adjust the size and/or shape of the implantable device 1102 (shown in FIGS. 10-12).

Figure 16:
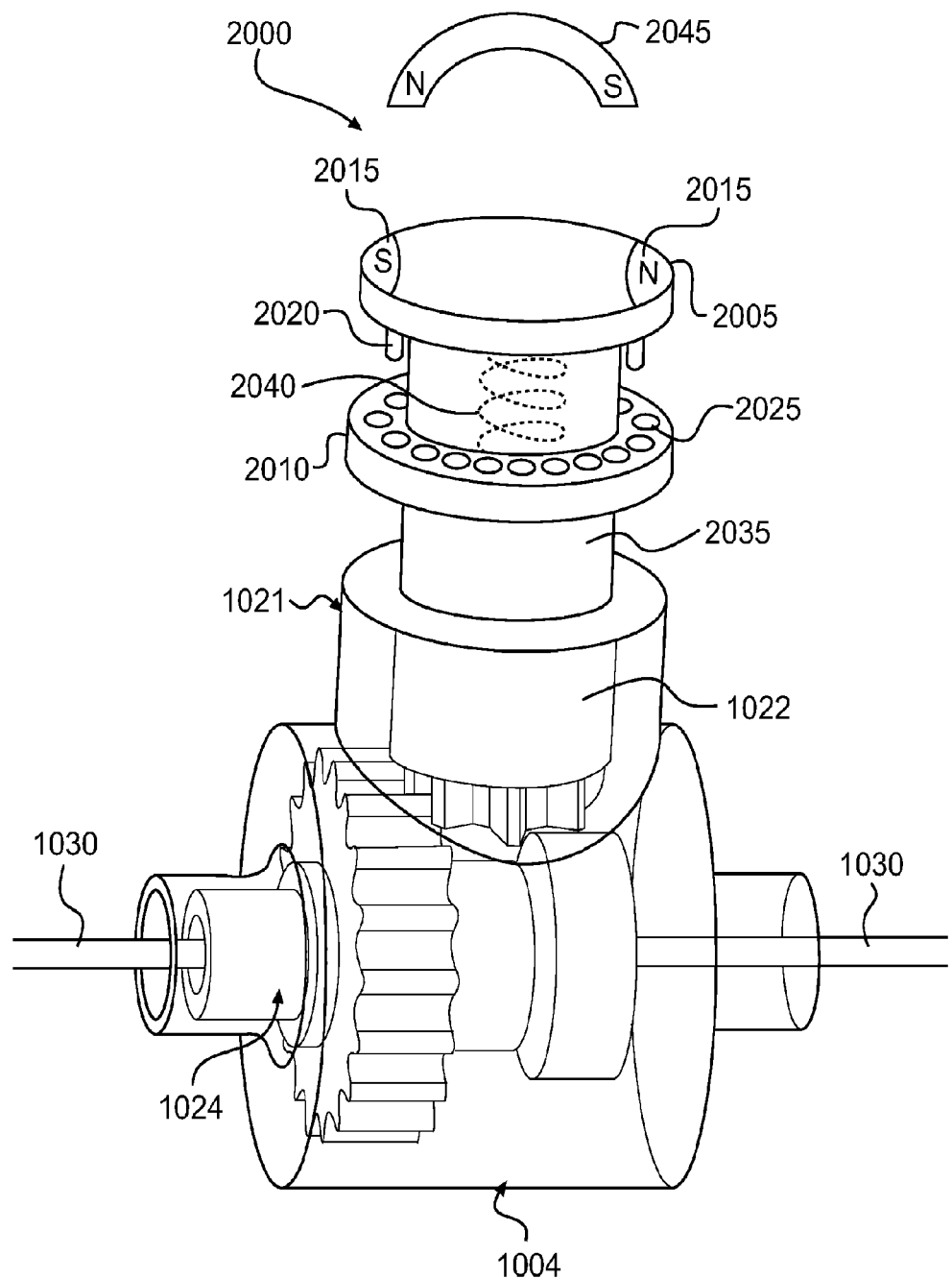
FIG. 16 is a schematic view of an embodiment of a long term adjustment system of the present invention coupled to an adjustable member of an implantable device.

FIG. 16 provides a more detailed view of the functional interaction between the long term adjustment system 2000 and the adjustable member 1004. As shown in FIG. 16, the adjustable member 1004 may include a docking port 1021, a pinion gear 1022, and a crown gear 1024. (The adjustable member 1004 is further discussed above with respect to FIGS. 8-12.) In some embodiments of the present invention, the shaft 2035 of the long term adjustment system 2000 can be removably or permanently coupled to the adjustable member 1004 via the docking port 1021. In other embodiments of the present invention, the pinion gear 1022 may be eliminated from the adjustable member 1004, and the distal end of the shaft 2035 may serve as a pinion gear when the shaft 2035 is coupled to the docking port 1021. FIG. 16 shows the long term adjustment system 2000 in an activated position. Therefore, rotating the activating magnet 2045 outside the patient's body will cause a corresponding rotation of the upper element 2005 and the shaft 2035. The rotation of the shaft 2035 will cause the pinion gear 1022 to engage the crown gear 1024, and the resulting rotation of the crown gear 1024 will rotate an inner cable 1030 in the same direction. As discussed above with respect to FIGS. 10-12, the rotation of the inner cable 1030 will, depending on the direction of rotation, cause the circumference of the implantable device 1102 (shown in FIGS. 10-12) to increase or decrease in size. The desired size for the implantable device can be determined by monitoring the mitral valve during adjustment using echocardiography or other known diagnostic modalities. Once a desired size for the implantable device 1102 (shown in FIGS. 10-12) is achieved, the activating magnet 2045 can be removed from the area near the patient's body, and the force generated by the spring 2040 will cause the upper element 2005 to return to a locked position.

Figure 17:
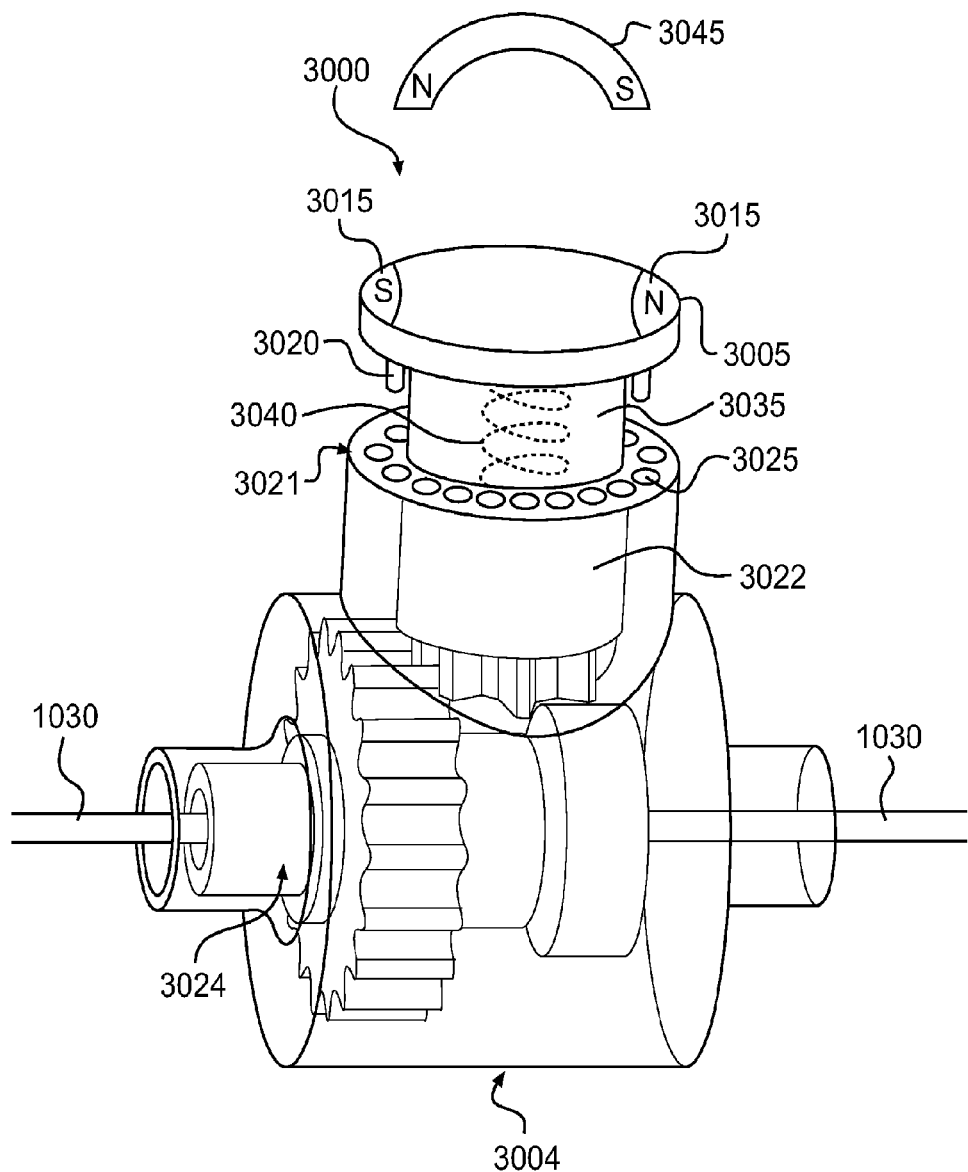
FIG. 17 is a schematic view of an embodiment of a long term adjustment system of the present invention coupled to an adjustable member of an implantable device.

In another embodiment of the present invention, FIG. 17 shows a long term adjustment system 3000 that comprises an upper element 3005 with a magnet, or other magnetic material, 3015 and retention pins 3020. This embodiment of the long term adjustment system does not have a lower element because a docking port 3021 includes retention holes 3025. The upper element 3005 is rotatably connected to an adjustable member 3004 via a shaft 3035. As shown in FIG. 17, the adjustable member 3004 may include a docking port 3021, a pinion gear 3022, and a crown gear 3024. The shaft 3035 includes a spring 3040 that is configured so that the force of the spring 3040 keeps the long term adjustment system 3000 in a locked position. The long term adjustment system 3000 is in the locked position when the retention pins 3020 of the upper element 3005 are engaged with the retention holes 3025 of the docking port 3021. When in the locked position, the upper element 3005 cannot move relative to the docking port 3021, and thus cannot activate the adjustable member 3004 of the implantable device 1102 (shown in FIGS. 10-12). Although not shown in FIG. 17, the long term adjustment system 3000 can have an optional outside covering.

As shown in FIG. 17, the long term adjustment system 3000 can be activated, without any entry into a patient's body, by placing an activating magnet 3045 near the area of the patient's body where the long term adjustment system 3000 is located and positioning the activating magnet 3045 so that an attractive force is generated between the activating magnet 3045 and the magnet 3015 in the upper element 3005. This positioning can be achieved using echocardiography or other known diagnostic modalities. The activating magnet 3045 can be any magnet that will attract the magnet 3015 in the upper element 3005 with a force sufficient to overcome the force of the spring 3040. As a result, when the activating magnet 3045 is positioned properly, the attractive force generated by the activating magnet 3045 will pull the upper element 3005 away from the docking port 3021, thus disengaging the retention pins 3020 from the retention holes 3025. Once the upper element 3005 has been disengaged from the docking port 3021, rotating the activating magnet 3045 outside the patient's body will cause a corresponding rotation of the upper element 3005 and the shaft 3035. The rotation of the shaft 3035 will cause the pinion gear 3022 to engage the crown gear 3024, and the resulting rotation of the crown gear 3024 will rotate an inner cable 1030 in the same direction. As discussed above with respect to FIGS. 10-12, the rotation of the inner cable 1030 will, depending on the direction of rotation, cause the circumference of the implantable device 1102 (shown in FIGS. 10-12) to increase or decrease in size. The desired size for the implantable device can be determined by monitoring the mitral valve during adjustment using echocardiography or other known diagnostic modalities. Once a desired size for the implantable device 1102 (shown in FIGS. 10-12) is achieved, the activating magnet 3045 can be removed from the area near the patient's body, and the force generated by the spring 3040 will cause the upper element 3005 to return to a locked position.

Figure 18:
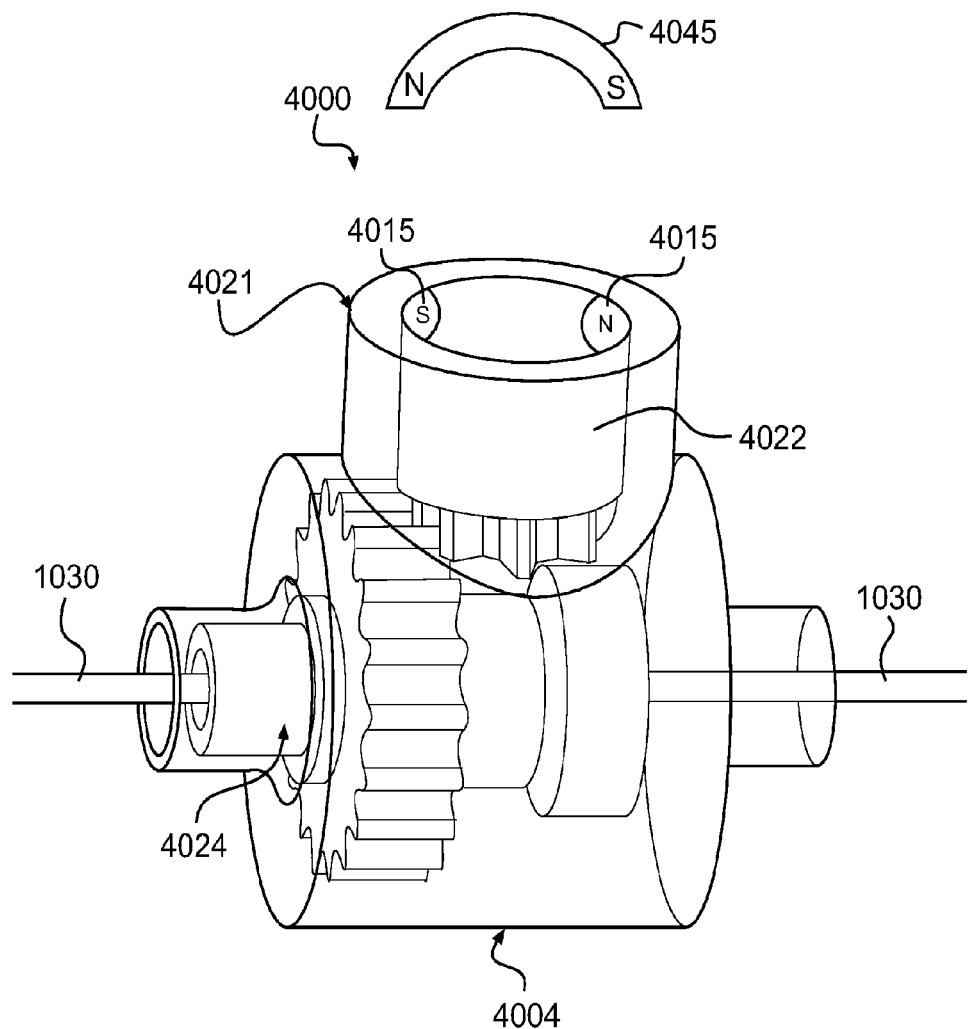
FIG. 18 is a schematic view of an embodiment of a long term adjustment system of the present invention integrated with an adjustable member of an implantable device.

In another embodiment of the present invention, FIG. 18 shows a long term adjustment system 4000. An adjustable member 4004 shown in FIG. 18 may include a docking port 4021, a pinion gear 4022, and a crown gear 4024. In this embodiment, the pinion gear 4022 includes a magnet or other magnetic material 4015. The long term adjustment system 4000 can be activated, without any entry into a patient's body, by placing an activating magnet 4045 near the area of the patient's body where the long term adjustment system 4000 is located and positioning the activating magnet 4045 so that an attractive force is generated between the activating magnet 4045 and the magnet 4015 in the pinion gear 4022. This positioning can be achieved using echocardiography or other known diagnostic modalities. The activating magnet 4045 can be any magnet that will attract the magnet 4015 in the pinion gear 4022 with a force sufficient to rotate the pinion gear 4022. As a result, rotating the activating magnet 4045 outside the patient's body will cause the pinion gear 4022 to engage the crown gear 4024, and the resulting rotation of the crown gear 4024 will rotate an inner cable 1030 in the same direction. As discussed above with respect to FIGS. 10-12, the rotation of the inner cable 1030 will, depending on the direction of rotation, cause the circumference of the implantable device 1102 (shown in FIGS. 10-12) to increase or decrease in size. The desired size for the implantable device can be determined by monitoring the mitral valve during adjustment using echocardiography or other known diagnostic modalities. Once a desired size for the implantable device 1102 (shown in FIGS. 10-12) is achieved, the activating magnet 4045 can be removed from the area near the patient's body, and no further adjustment will occur.

Figure 19:
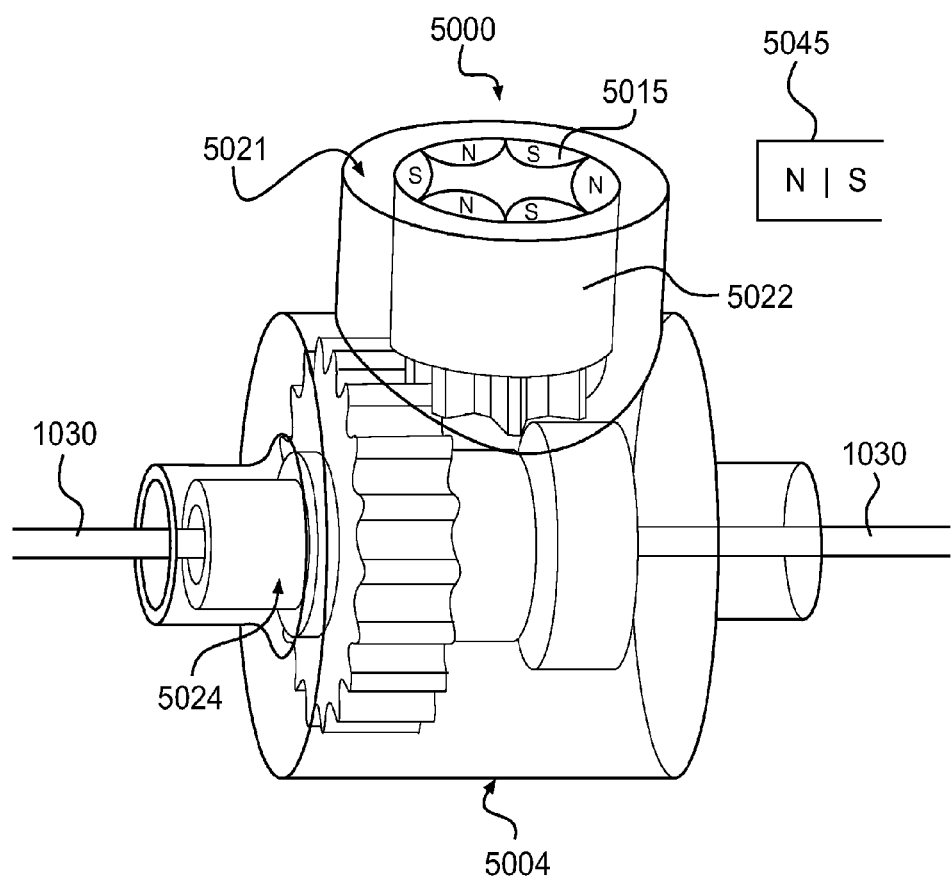
FIG. 19 is a schematic view of an embodiment of a long term adjustment system of the present invention integrated with an adjustable member of an implantable device.
Figure 20A:
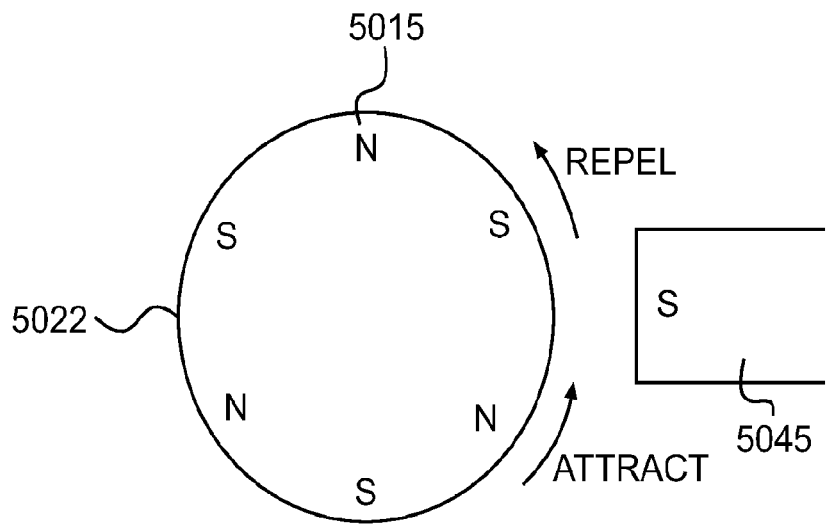
FIG. 20A is a schematic view of an embodiment of a pinion gear of the long term adjustment system of FIG. 19 being activated by an alternating magnet.
Figure 20B:
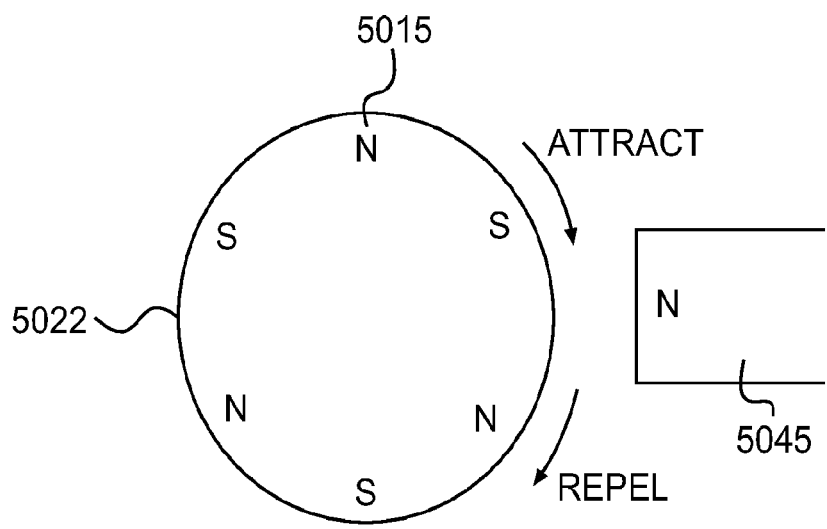
FIG. 20B is a schematic view of an embodiment of a pinion gear of the long term adjustment system of FIG. 19 being activated by an alternating magnet.

In another embodiment of the present invention, FIG. 19 shows a long term adjustment system 5000. An adjustable member 5004 may include a docking port 5021, a pinion gear 5022, and a crown gear 5024. In this embodiment, the pinion gear 5022 may include multiple magnets or other magnetic material 5015 positioned so that the poles along the outside edge of the pinion gear 5022 alternate polarity (i.e., N-S-N-S), as shown in FIG. 19. The long term adjustment system 5000 can be activated, without any entry into a patient's body, by positioning an alternating magnet 5045 near the area of the patient's body where the long term adjustment system 5000 is located. This positioning can be achieved using echocardiography or other known diagnostic modalities. The alternating magnet 5045 can be any alternating magnet that will attract the magnets 5015 in the pinion gear 5022 with a force sufficient to rotate the pinion gear 5022. As shown in FIGS. 20A and 20B, the alternating magnet 5045 will attract the closest magnet 5015 with a different polarity and repel the closest magnet 5015 with a similar polarity, which will cause the pinion gear 5022 to begin rotating in either a clockwise or counter-clockwise direction, depending on the initial configuration of the magnets 5015 and the initial polarity of the alternating magnet 5045. Reversing the polarity of the alternating magnet 5045 each time one of the magnets 5015 passes by it will cause the pinion gear 5022 to continue rotating. Thus, as shown in FIG. 19, alternating the polarity of the alternating magnet 5045 will cause the pinion gear 5022 to engage the crown gear 5024, and the resulting rotation of the crown gear 5024 will rotate an inner cable 1030 in the same direction. As discussed above with respect to FIGS. 10-12, the rotation of the inner cable 1030 will, depending on the direction of rotation, cause the circumference of the implantable device 1102 (shown in FIGS. 10-12) to increase or decrease in size. The desired size for the implantable device can be determined by monitoring the mitral valve during adjustment using echocardiography or other known diagnostic modalities. Once a desired size for the implantable device 1102 (shown in FIGS. 10-12) is achieved, the alternating magnet 5045 can be removed from the area near the patient's body, and no further adjustment will occur.

Figure 21:
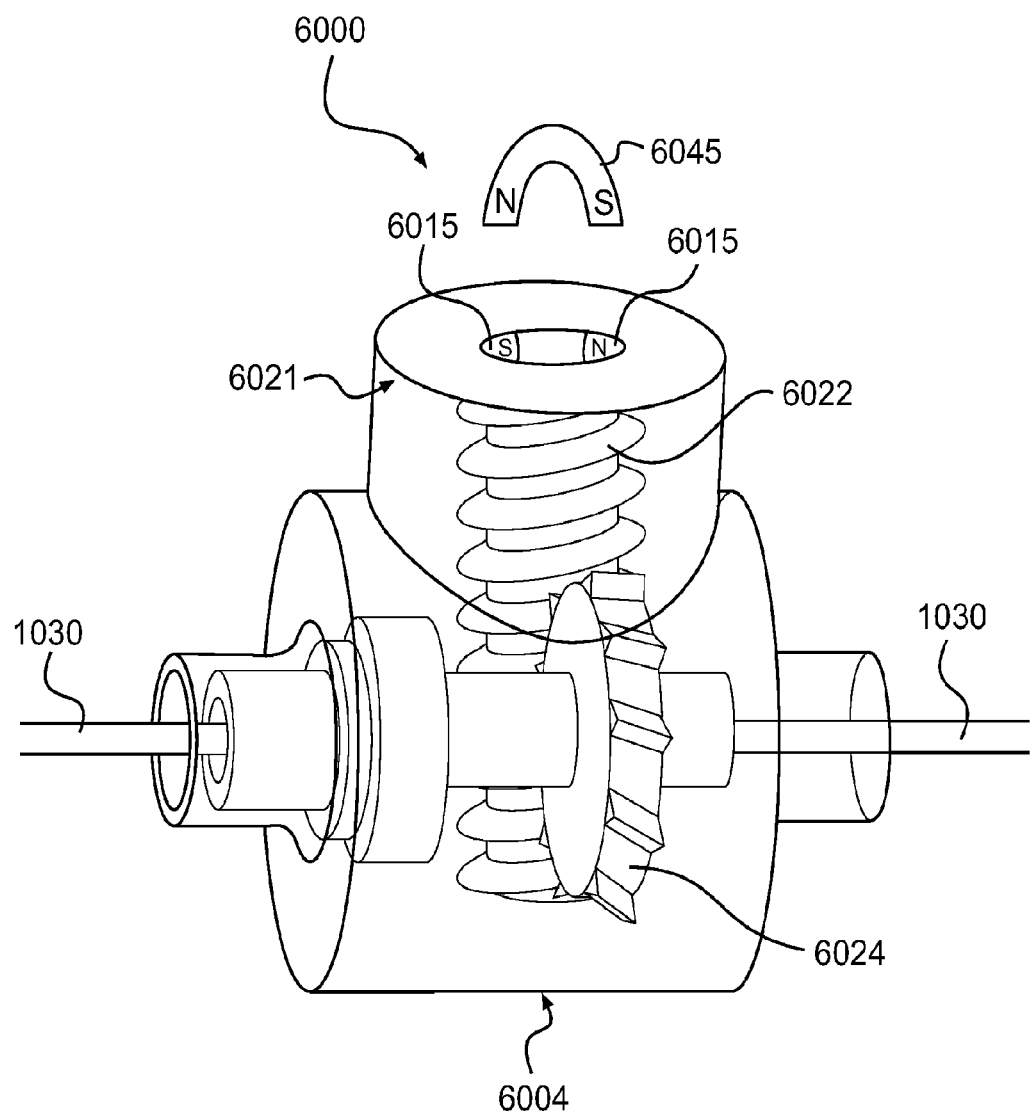
FIG. 21 is a schematic view of an embodiment of a long term adjustment system of the present invention with an adjustable member of an implantable device.

In another embodiment of the present invention, FIG. 21 shows a long term adjustment system 6000. An adjustable member 6004 shown in FIG. 21 may include a docking port 6021, a worm 6022, and a worm gear 6024. The worm 6022 includes a magnet or other magnetic material 6015. The long term adjustment system 6000 can be activated, without any entry into a patient's body, by placing an activating magnet 6045 near the area of the patient's body where the long term adjustment system 6000 is located and positioning the activating magnet 6045 so that an attractive force is generated between the activating magnet 6045 and the magnet 6015 in the worm 6022. This positioning can be achieved using echocardiography or other known diagnostic modalities. The activating magnet 6045 can be any magnet that will attract the magnet 6015 in the worm 6022 with a force sufficient to rotate the worm 6022. As a result, rotating the activating magnet 6045 outside the patient's body will cause the worm 6022 to engage the worm gear 6024, and the resulting rotation of the worm gear 6024 will rotate an inner cable 1030 in the same direction. As discussed above with respect to FIGS. 10-12, the rotation of the inner cable 1030 will, depending on the direction of rotation, cause the circumference of the implantable device 1102 (shown in FIGS. 10-12) to increase or decrease in size. The desired size for the implantable device can be determined by monitoring the mitral valve during adjustment using echocardiography or other known diagnostic modalities. Once a desired size for the implantable device 1102 (shown in FIGS. 10-12) is achieved, the activating magnet 6045 can be removed from the area near the patient's body, and no further adjustment will occur.

Figure 22A:
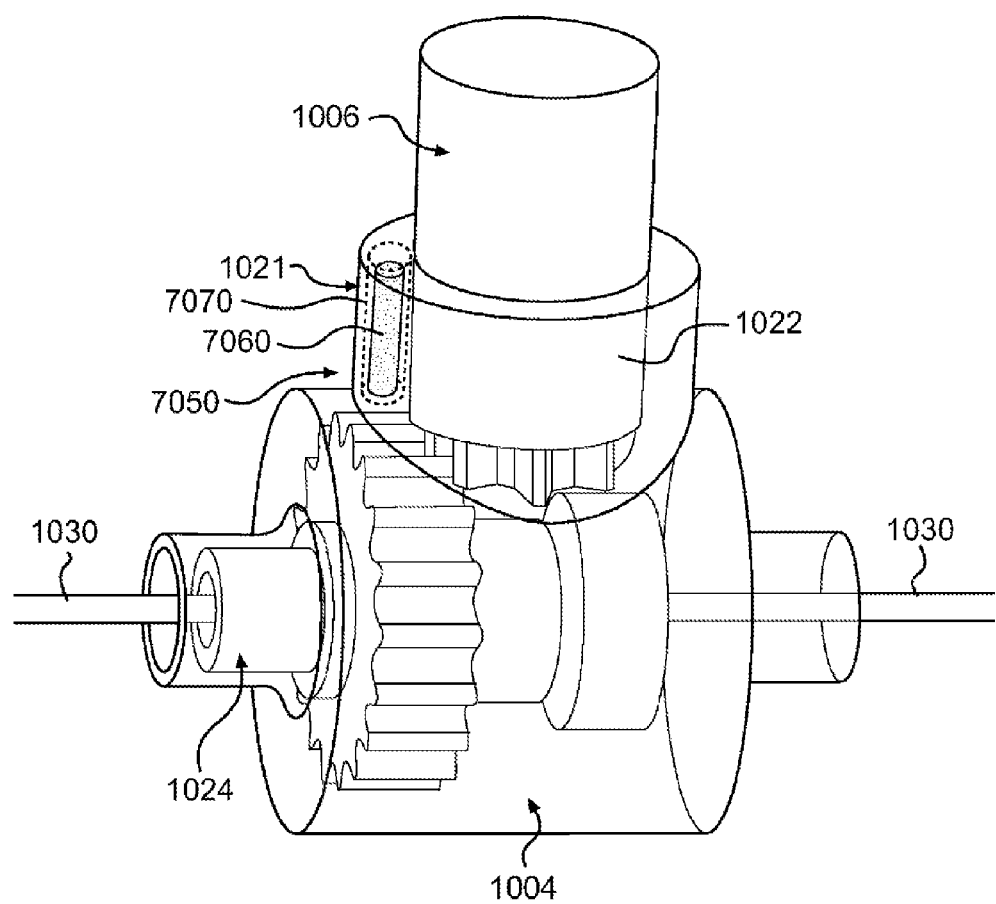
FIG. 22A is a schematic view of an embodiment of a locking mechanism for the long term adjustment system of the present invention, shown in an unlocked position.
Figure 22B:
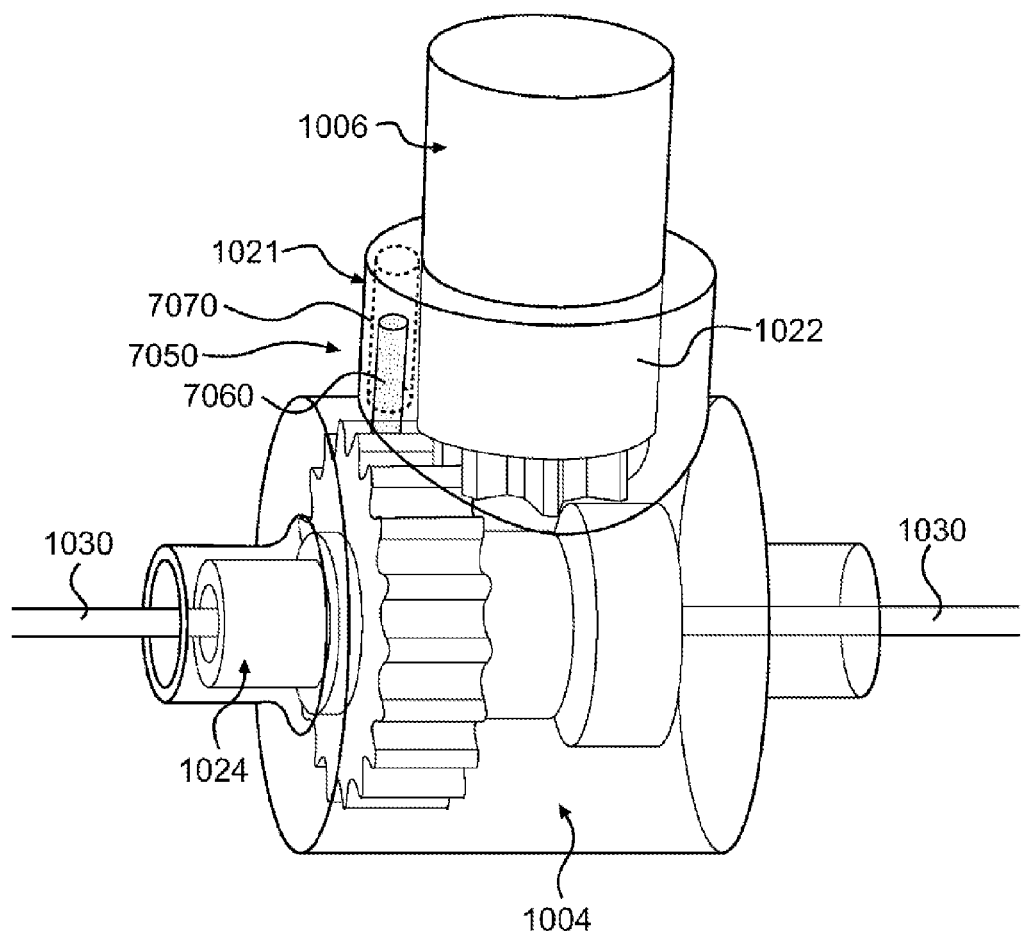
FIG. 22B is a schematic view of an embodiment of a locking mechanism for the long term adjustment system of the present invention, shown in a locked position.

FIGS. 22A and 22B show one embodiment of a locking mechanism 7050 that can be used in connection with the long term adjustment system previously described herein. The locking mechanism 7050 shown in FIGS. 22A and 22B allows a person who has an implantable device with a long term adjustment system to undergo procedures involving the application of magnetic fields, such as magnetic resonance imaging ("MRI"), without it causing any unwanted adjustment of the implantable device. FIGS. 22A and 22B show an adjustable member 1004 of an implantable device 1102 (shown in FIGS. 10-12) that contains the locking mechanism 7050. Although the long term adjustment system of FIGS. 13-21 is not depicted in FIGS. 22A and 22B, it is contemplated that the locking mechanism 7050 can be incorporated into any of the embodiments of the long term adjustment system previously described herein. The locking mechanism 7050 comprises a gear locking pin 7060 and a pin housing 7070, which are both incorporated into the docking port 1021 of the adjustable member 1004. The gear locking pin 7060 is preferably made of an inert material with a high atomic weight, such as gold, and is coated with a material, such as titanium, that is compatible with the crown gear 1024. Furthermore, the gear locking pin 7060 and the pin housing 7070 are designed so that the gear locking pin 7060 can move freely within the pin housing 7070.

FIG. 22A shows the locking mechanism 7050 in an unlocked, or inactive, position. The gear locking pin 7060 is completely within the pin housing 7070, and, as such, it is not in contact with the crown gear 1024 of the adjustable member 1004. Therefore, when the locking mechanism 7050 is in unlocked position, the crown gear 1024 is able to rotate in response to activation of the long term adjustment system and thereby cause the desired adjustment of the implantable device. FIG. 22B shows the locking mechanism 7050 in the locked, or active, position. The locking mechanism 7050 is positioned within the adjustable member 1004 so that when a person lays down in a supine position, gravity will cause the gear locking pin 7060 to move downward within the pin housing 7070 until it contacts the crown gear 1024. When the gear locking pin 7060 is in contact with the crown gear 1024, it prevents the crown gear 1024 from rotating. As a result, the inner cable 1030 also cannot move and the implantable device cannot be adjusted using the long term adjustment system. Thus, the locking mechanism 7050 allows a person to undergo an MRI, or any other procedure involving the use of magnetic fields, while in the supine position, without the magnetic fields causing any unwanted adjustment of the implantable device.

The locking mechanism 7050 can be designed to ensure that the gear locking pin 7060 is moveable within the pin housing 7070. This can be accomplished, for example, by minimizing the contact surface area between the gear locking pin 7060 and the pin housing 7070. This design reduces the frictional force exerted by the pin housing 7070 on the gearing locking pin 7060, allowing the gear locking pin 7060 to move more freely within the pin housing 7070. In another embodiment of the locking mechanism 7050, it is contemplated that, if needed, the application of external forces, such as sound waves, can be used to facilitate movement of the gear locking pin 7060 within the pin housing 7070. Such external forces can be used to drive the gear locking pin 7060 into contact with the crown gear 1024, as well as to pull the gear locking pin 7060 away from the crown gear 1024 and into the pin housing 7070.

The cardiac applications of the present invention that were discussed herein are only some examples of the applications of the present invention. It is contemplated that the invention described herein and the methods for its use have many other applications in the broad fields of medicine and surgery. For example, the present invention can be used for the treatment of gastric reflux, morbid obesity, anal incontinence, urinary incontinence, anastomotic strictures, arterial stenosis, ductal strictures, tricuspid valvular dysfunction, and cervical incompetence.

While exemplary embodiments of the invention have been shown and described herein, it will be obvious to those skilled in the art that such embodiments are provided by way of example only. Numerous insubstantial variations, changes, and substitutions will now be apparent to those skilled in the art without departing from the scope of the invention disclosed herein by the Applicants. Accordingly, it is intended that the invention be limited only by the spirit and scope of the claims, as they will be allowed.

The invention claimed is:

1. A system for adjusting the dimensions of an adjustable implant for altering physiologic fluid flow through an anatomical orifice or lumen of a patient, comprising:
   an adjustable implant comprising an adjustable ring having a circumference, an adjustable member coupled to the ring for changing upon operation thereof the size or shape of the circumference of the adjustable ring for altering physiologic fluid flow through the adjustable ring;
   a magnetic material functionally connected to the adjustable member to effect the operation of the adjustable member;
   an activating magnet for effecting the adjustment of the adjustable ring by the adjustable member upon being magnetically coupled by an attraction force to the magnetic material, whereby the size or shape of the circumference of the adjustable ring is changed by the adjustable member for altering the physiologic fluid flow therethrough and through an anatomical orifice or lumen of a patient; and
   a locking mechanism having an unlocked configuration for permitting adjustment of the adjustable implant by the adjustable member and a locked configuration for preventing adjustment of the adjustable implant by the adjustable member, the locking mechanism comprising an upper element having a plurality of retention pins extending therefrom, a lower element having a plurality of retention holes configured to receive the plurality of retention pins, and a spring configured to maintain the plurality of retention pins engaged with the plurality of retention holes whereby the locking mechanism is in the locked configuration, wherein the retention pins are maintained within the retention holes by operation of the spring when the locking mechanism is in the locked configuration, and wherein the retention pins are withdrawn from within the retention holes when the locking mechanism is in the unlocked configuration by the attraction force created by magnetic coupling of the magnet material to the activating magnet, and wherein the attraction force pulls the plurality of retention pins towards the activating magnet to cause the plurality of pins to be withdrawn from the plurality of retention holes.

2. The system of claim 1, wherein the locking mechanism is constructed to be deactivated into the unlocked configuration by the activating magnet.

3. The system of claim 1, wherein the locking mechanism comprises a locking pin moveable with a pin housing.

4. The system of claim 1, wherein the magnetic material comprises a plurality of magnets.

5. The system of claim 4, wherein the plurality of magnets are arranged with alternating polarity.

6. The system of claim 1, wherein the adjustable member includes a docking port.

7. The system of claim 6, wherein the locking mechanism for preventing adjustment of the adjustable implant is coupled to the docking port.

8. The system of claim 1, further including a shaft rotationally coupling the upper element to the adjustable member, the shaft passing through the lower element.

9. The system of claim 1, wherein the magnetic material is disposed on the upper element.

10. A system for adjusting the dimensions of an adjustable implant for altering physiologic fluid flow through an anatomical orifice or lumen of a patient, comprising:
    an adjustable implant comprising an adjustable ring having a circumference, an adjustable member coupled to the ring for changing upon operation thereof the size or shape of the circumference of the adjustable ring for altering physiologic fluid flow through the adjustable ring;
    a magnetic material functionally connected to the adjustable member to effect the operation of the adjustable member;
    an activating magnet for effecting the adjustment of the adjustable ring by the adjustable member upon being magnetically coupled by an attraction force to the magnetic material, whereby the size or shape of the circumference of the adjustable ring is changed by the adjustable member for altering the physiologic fluid flow therethrough and through an anatomical orifice or lumen of a patient; and
    a locking mechanism for preventing adjustment of the adjustable implant by the adjustable member, the locking mechanism comprising an upper element having at least one retention pin extending therefrom, a lower element having at least one retention hole configured to receive the at least one retention pin, and a shaft attached to the upper element rotationally coupling the upper element directly to the adjustable member, the shaft passing through the lower element, wherein the attraction force created by magnetic coupling of the magnetic material to the activating magnet is sufficient to withdraw the at least one retention pin from the at least one retention hole thereby allowing adjustment of the adjustable implant by the activating magnet, and wherein the attraction force causes the at least one retention pin to be withdrawn from the at least one retention hole by attraction of one of the elements to the activating magnet.

11. The system of claim 10, further including a spring arranged between the upper element and lower element.

12. A system for adjusting the dimensions of an adjustable implant for altering physiologic fluid flow through an anatomical orifice or lumen of a patient, comprising:
    an adjustable implant comprising an adjustable ring having a circumference, an adjustable member coupled to the ring for changing upon operation thereof the size or shape of the circumference of the adjustable ring for altering physiologic fluid flow through the adjustable ring;
    a magnetic material functionally connected to the adjustable member to effect the operation of the adjustable member;
    an activating magnet for effecting the adjustment of the adjustable ring by the adjustable member upon being magnetically coupled by an attraction force to the magnetic material, whereby the size or shape of the circumference of the adjustable ring is changed by the adjustable member for altering the physiologic fluid flow therethrough and through an anatomical orifice or lumen of a patient; and a locking mechanism for preventing adjustment of the adjustable implant by the adjustable member, the locking mechanism comprising an upper element having at least one retention pin extending therefrom, a lower element having at least one retention hole configured to receive the at least one retention pin when the locking mechanism is in a locked configuration, and the at least one retention pin withdrawn from the at least one retention hole when the locking mechanism is in an unlocked configuration by the attraction force created by magnetic coupling of the magnet material to the activating magnet, and wherein the attraction force causes the at least one retention pin to be withdrawn from the at least one retention hole by attraction of one of the elements to the activating magnet.

* * * * *